United States Patent [19]

Kritzer

[11] 4,062,358
[45] Dec. 13, 1977

[54] RESPIRATORS

[76] Inventor: Richard W. Kritzer, 5800 N. Pulaski Road, Chicago, Ill. 60646

[21] Appl. No.: 679,010

[22] Filed: Apr. 21, 1976

[51] Int. Cl.² .......................................... A61M 16/00
[52] U.S. Cl. ................................. 128/208; 128/203; 128/142.3; 128/209; 272/99
[58] Field of Search ............... 128/208, 206, 209, 210, 128/147, 145.6, 145 R, 142 R, 142.3, 184, 203; 46/180, 181; 272/99 R

[56] References Cited

U.S. PATENT DOCUMENTS

| | | | |
|---|---|---|---|
| 2,269,823 | 1/1942 | Kreiselman | 128/184 |
| 2,918,917 | 12/1959 | Emerson | 128/145.6 |
| 3,906,996 | 9/1975 | DePass et al. | 128/210 |
| 3,955,313 | 5/1976 | Faulk | 46/180 |

*Primary Examiner*—John D. Yasko
*Assistant Examiner*—Henry J. Recla
*Attorney, Agent, or Firm*—Emrich, Root, O'Keeffe & Lee

[57] ABSTRACT

A respirator through which a person may breath air or a mixture of air and oxygen, and which vibrates the material passing through the respirator during inhalation and exhalation in such a manner as to vibrate the cilia in the lungs of the person breathing through the respirator.

10 Claims, 13 Drawing Figures

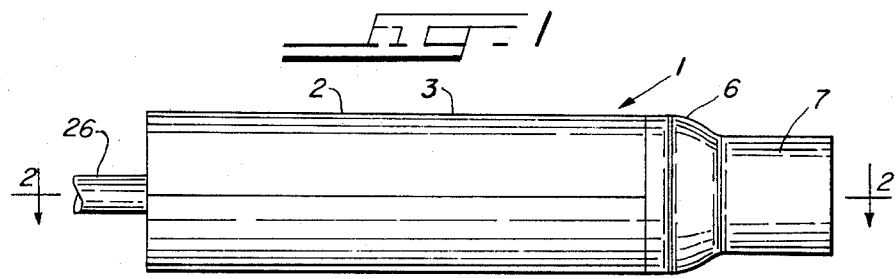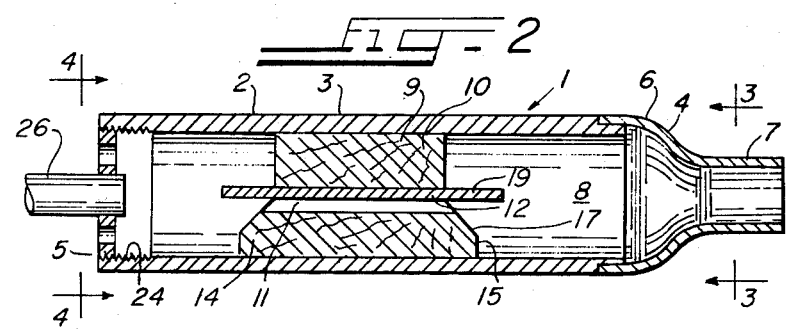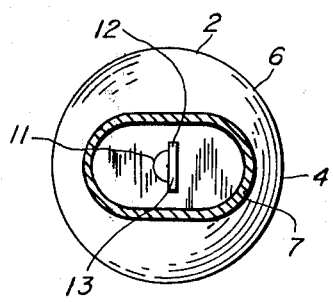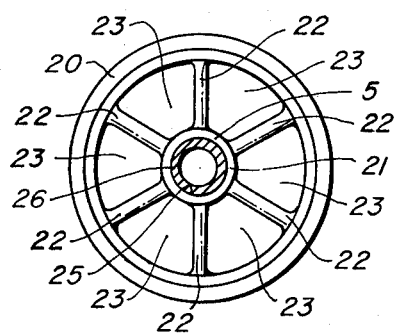

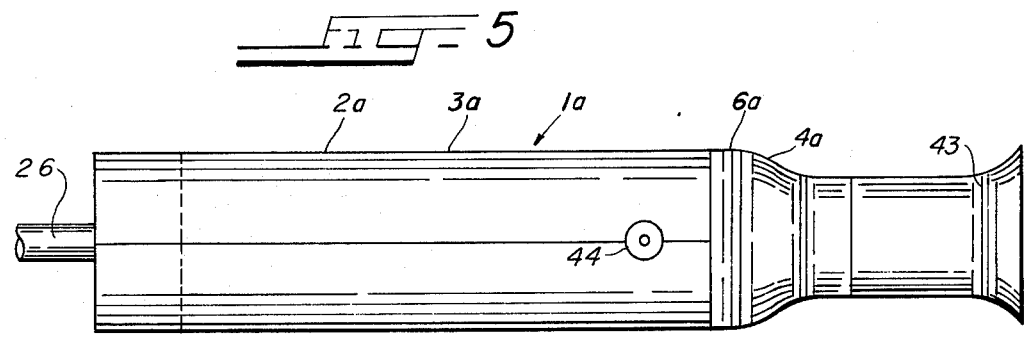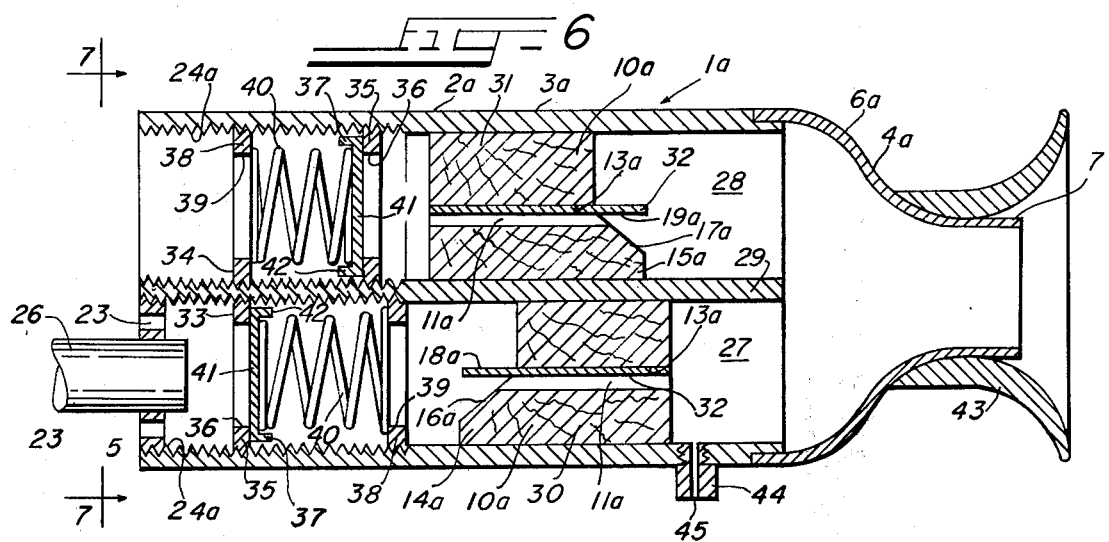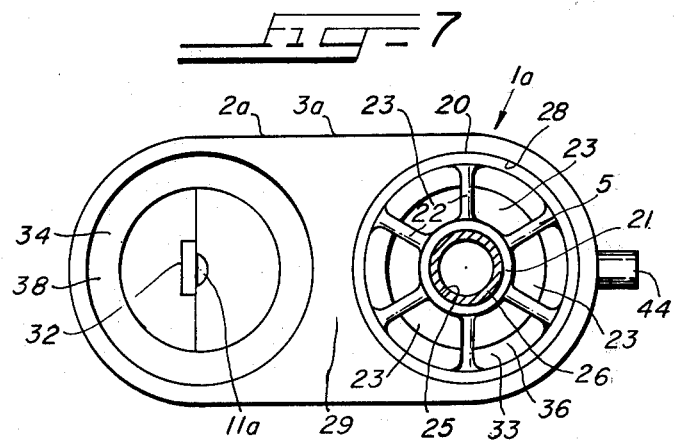

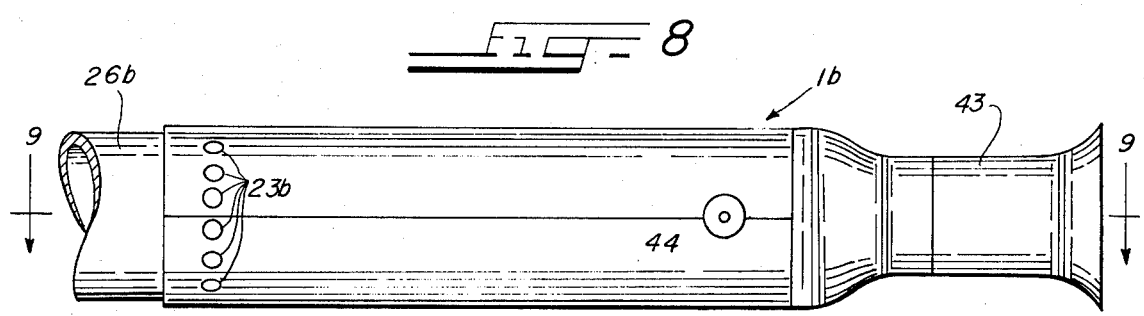
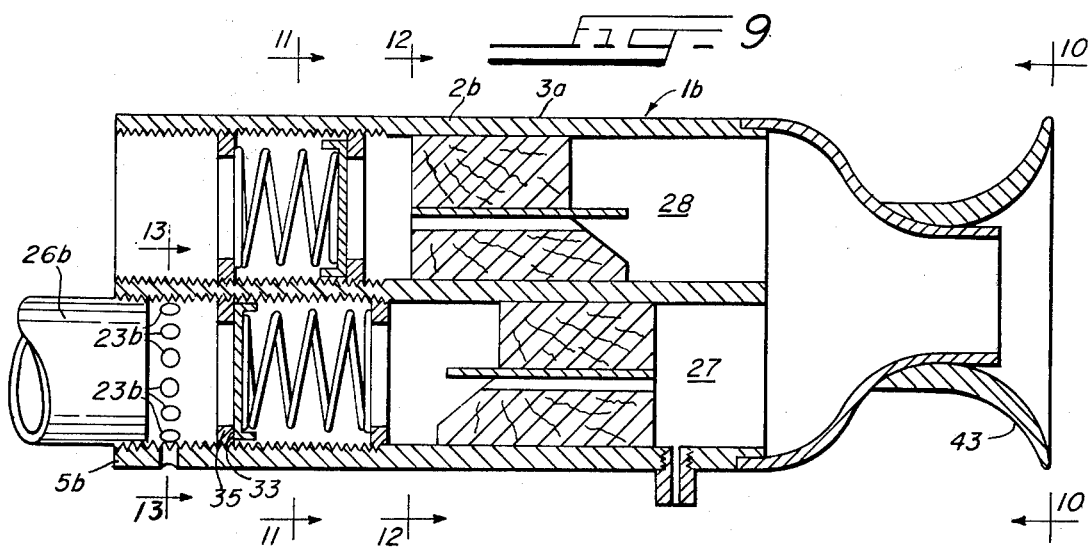
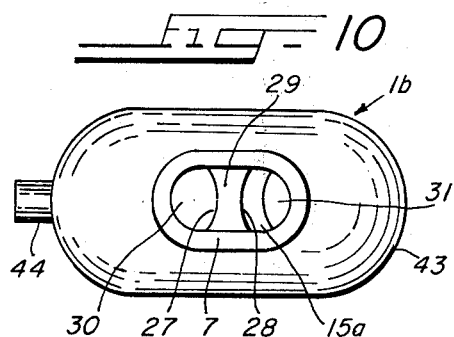 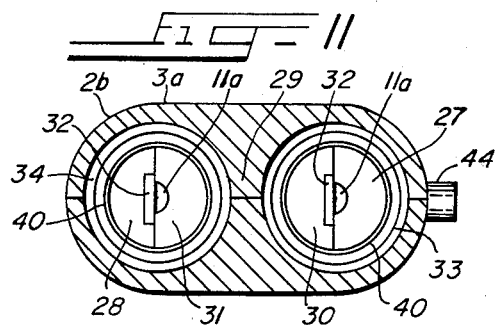
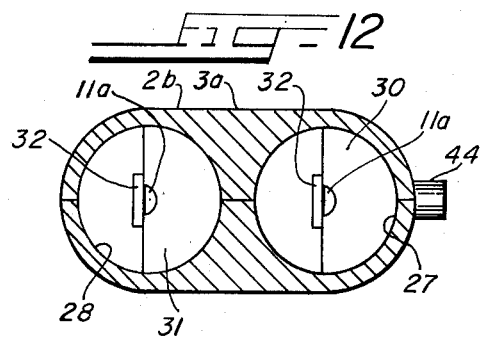 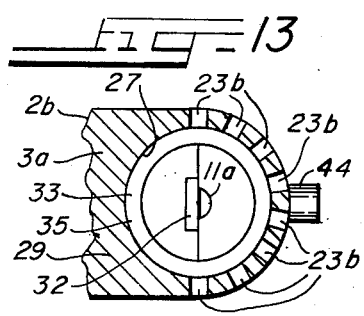

RESPIRATORS

BACKGROUND OF THE INVENTION

This invention relates to respirators, and, more particularly, to respirators that are particularly well adapted for use by persons suffering from emphysema, and the like.

It is a primary object of the present invention to afford a novel respirator.

Another object of the present invention is to afford a novel respirator which is effective to vibrate the material passing therethrough in such a manner that it is effective to vibrate the cilia in the lungs of the person breathing through the respirator.

A further object is to afford a novel respirator which is effective to so vibrate the material passing therethrough both on inhalation and exhalation.

Many persons suffer from ailments, such as, for example, emphysema, or the like, wherein the cilia in the lungs have become flattened down or clogged with mucous, or the like. It is my opinion, which seems to have been borne out by experimentation, that vibration of air passing into and out of the lungs of the persons suffering from the aforementioned conditions is effective to cause cilia, which have been flattened down, to be vibrated into an upstanding position, and to cause cilia which have been clogged with mucous, to be at least partially unclogged. When oxygen being breathed by such a person is vibrated in accordance with my present invention better utilization of the oxygen seems to be effected than when it is not so vibrated.

Respirators, which are effective to vibrate the material passing therethrough during both inhalation and exhalation, have been heretofore known in the art, being disclosed, for example, in my co-pending application for U.S. States Letters Pat., Ser. No. 613,176, filed Sept. 15, 1975. Vibrators of the type disclosed in my aforementioned co-pending patent application have proven to be very effective. However, it is an object of the present invention to afford improvements over respirators of the type disclosed in the aforementioned co-pending patent application.

Insofar as is known, no one, prior to my invention of the respirator disclosed in my aforementioned co-pending application, Ser. No. 613,176, has afforded a respirator, or the like, through which a person can inhale and exhale, and which is effective, during such inhalation and exhalation to vibrate the air passing into and out of the persons lungs.

Certain articles, of course, heretofore known in the art, such as, for example, musical instruments; "Bronx cheer" toys such as the toy shown in U.S. Pat. No. 628,870; and duck calls or goose calls, such as the goose call shown in U.S. Pat. No. 2,730,836, have caused air, blown through the article to vibrate, thus causing sound to be emitted from the article. However, insofar as is known this has not, prior to my invention of the respirator disclosed in my aforementioned co-pending application, Ser. No. 613,176, been true with respect to, or a purpose of a respirator. In fact, insofar as is known, no one, other than myself, has heretofore conceived a respirator of the aforementioned type.

Another object of the present invention is to afford a novel respirator which may be quickly and easily attached to a source of oxygen, for inhalation of oxygen by a patient using the respirator, and which, when it is so connected, is effective to vibrate the oxygen, in a sound-emitting manner, during both inhalation and exhalation by the person using the respirator.

Yet another object of the present invention is to afford a novel respirator of the aforementioned type, which, when it is so connected to a source of oxygen, is effective, in a novel and expeditous manner, to permit air to pass thereinto, to mix with and supplement the oxygen during inhalation through the respirator.

A further object of the present invention is to afford a novel respirator of the aforementioned type wherein the flow of air into the respirator, during inhalation, is sufficient to cause effective sound-emitting vibrations of the material passing through the respirator, during both inhalation and exhalation, irrespective of the amount of flow of oxygen into the respirator, and irrespective of whether or not the flow of oxygen into the respirator is completely cut off.

Another object of the present invention is to afford a novel respirator, which is effective to produce the aforementioned sound-emitting vibrations of material passing therethrough, both during inhalation and exhalation, irrespective of whether or not the respirator is connected to a tube or any other device for feeding oxygen thereinto.

Another object of the present invention is to afford a novel respirator of the aforementioned type, which is practical and efficient in operation, and which may be readily and economically produced commercially.

Other and further objects of the present invention will be apparent from the following description and claims and are illustrated in the accompanying drawings which, by way of illustration, show the preferred embodiments of the present invention and the principles thereof and what I now consider to be the best mode in which I have contemplated applying these principles. Other embodiments of the invention embodying the same or equivalent principles may be used and structural changes may be made as desired by those skilled in the art without departing from the present invention and purview of the appended claims.

SUMMARY OF THE INVENTION

A respirator which is particularly well adapted for use by persons suffering from emphysema, or the like, and which embodies a housing having a mouthpiece at one end thereof, through which a person may inhale and exhale, with the other end of the housing being adapted to be connected, if desired, by a suitable tube, or the like, to a source of oxygen, with the last mentioned end of the housing being adapted to permit the flow of air thereinto, either as a supplement to the oxygen, or as a replacement thereof, with vibrator mechanism being mounted in the housing in such position that, as a person inhales and exhales through the mouthpiece, and, therefore, through the respirator, the air or the mixture of air and oxygen passing through the respirator during inhalation, and the material passing through the respirator during exhalation, is caused to vibrate in such a manner as to cause the cilia in the lungs of the person breathing through the respirator to vibrate.

DESCRIPTION OF THE DRAWINGS

In the drawings:

FIG. 1 is a side elevational view of a respirator embodying the principles of the present invention;

FIG. 2 is a longitudinal sectional view taken substantially along the line 2—2 in FIG. 1;

FIG. 3 is a detail sectional view taken substantially along the line 3—3 in FIG. 2;

FIG. 4 is an end view of the respirator shown in FIG. 1, looking in the direction of the arrows 4—4 in FIG. 2;

FIG. 5 is a side elevational view, similar to FIG. 1, but showing a modified form of the present invention;

FIG. 6 is a longitudinal sectional view taken substantially along the line 6—6 in FIG. 5;

FIG. 7 is an end view of the respirator shown in FIG. 5, looking in the direction of the arrows 7—7 in FIG. 6;

FIG. 8 is a side elevational view, similar to FIG. 5, but showing another form of the present invention;

FIG. 9 is a longitudinal sectional view taken substantially along the line 9—9 in FIG. 8;

FIG. 10 is an end view of the respirator shown in FIG. 8, looking in the direction of the arrows 10—10 in FIG. 9;

FIG. 11 is a detail sectional view taken substantially along the line 11—11 in FIG. 9;

FIG. 12 is a detail sectional view taken substantially along the line 12—12 in FIG. 9; and FIG. 13 is a fragmentary, detail sectional view taken substantially along the line 13—13 in FIG. 9.

DESCRIPTION OF THE EMBODIMENTS SHOWN HEREIN

A respirator or breathing unit 1 is shown in FIGS. 1-4, inclusive, of the drawings, to illustrate the presently preferred embodiment of the present invention.

The respirator 1 embodies an elongated, tubular housing 2, which is substantially round in transverse cross section. The housing 2 embodies an elongated, tubular body portion 3, an end portion or end cap 4 mounted on one end of the body portion 3, and a supporting member 5 disposed at the other end of the body portion 3, FIGS. 1 and 2. The end cap 4 embodies an inner end portion 6, mounted on one end of the body portion 3 in surrounding relation thereto, FIG. 2, and an outer end portion 7, which is smaller in cross sectional size than the inner end portion 6, and affords a mouthpiece which may be inserted into the mouth of a person breathing through the respirator. Preferably, the mouthpiece 7 is substantially eliptical in transverse shape so as to lend itself to ready sealing engagement with the lips of the person in whose mouth it is disposed.

The body portion 3 has a passageway 8 extending longitudinally, axially therethrough. A vibrator 9 is mounted in the passageway 8 in spaced relation to the cap 4 and the supporting member 5, FIG. 2. The vibrator 9 embodies an elongated body portion 10, having a passageway 11 extending longitudinally therethrough. The passageway 11 is substantially semi-circular in transverse cross section, FIG. 3, and an elongated reed 12, which is substantially rectangular in transverse cross section, is mounted at one side of the passageway 11 in a channel 13, which extends longitudinally through the body portion 10 in adjacent relation to the passageway 11. The reed 12 preferably is disposed in the channel 13 with a force fit, and, if desired, may be further secured to the body portion 10, in which it is mounted, by suitable means, such as, for example, an adhesive, not shown.

The body portion 10 of the vibrator 9 has two tongues 14 and 15 which project outwardly beyond the respective ends of the passageway 11, the faces 16 and 17 of the tongues 14 and 15, respectively, which face toward the reed 12, sloping outwardly away from the passageway 11 at an acute angle to the longitudinal axis of the latter.

The reed 12 has two end portions 18 and 19, which project outwardly away from the body portion 10 of the vibrator 9 toward the supporting member 5 and the cap 4, respectively. With the vibrator 9 constructed in the aforementioned manner and mounted in the passageway 8 material such as air, or a mixture of air and oxygen passing through the vibrator 9 from the supporting member 5 to the mouthpiece 7 will cause the end portion 18 of the reed 12 to be rapidly vibrated and thus cause vibrations to occur in the material in the respirator, and in the air in the trachea and lungs of the person breathing through the respirator 1; and air passing through the vibrator 9 from the mouthpiece 7 to the supporting member 5 will cause the end portion 19 of the reed 12 to be rapidly vibrated, and thus cause vibrations to occur in the material in the respirator, and in the air in the trachea and lungs of the person breathing through the respirator. Preferably, the vibrations thus caused to occur in the air, or mixture of air and oxygen, passing through the respirator are at such a frequency as to cause sound, which is audible to the human ear to emanate from the respirator 1. One reason that this is preferred is that it affords a means for monitoring the proper operation of the respirator 1, not only by the person who is breathing through the respirator 1, but also by another person, such as an attendant or nurse, the person monitoring the same being able to determine whether vibrations are being set up during inhalation and exhalation through the respirator 1 by the presence or absence of sound emanating therefrom. Another reason that I prefer that vibrations emanating from the respirator 1 be of a frequency audible to the human ear is that vibrations in the frequencies audible to the human ear appear to cause vibrations of the air in the lungs of a person breathing through the respirator 1 which are most effective in beneficially vibrating the cilia in the lungs of the person using the respirator. This is particularly true in the lower ranges of the frequencies audible to the human ear, and, as a result, I prefer that, as is true with respect to the vibrators in the respirators disclosed in my aforementioned co-pending application, Ser. No. 613,716, the vibrator 9 be such that the vibrations caused by the inhalation and exhalation of a person using my novel respirator 1 be not substantially less than one hundred vibrations per second and non substantially more than three hundred vibrations per second.

The reed 12 of the vibrator 9 may be made of any suitable material, but, preferably, is made of a suitable composition material, such as, for example, a composition of hard rubber, or a suitable plastic material, such as, for example, polystyrene. Similarly, the body portion 10 of the vibrator 9 may be made of any suitable material, but, preferably, is made of a suitable, relatively hard wood, such as, for example, mahogony, or the like.

Also, the body portion 3 and the end cap 4 of the housing 2 may be made of any suitable material, such as, for example, a suitable plastic material, such as, for example, polypropylene, polyethylene or polystyrene, but, preferably, they are made of a suitable wood, such as, for example, white pine, or the like. In addition, the supporting member 5 may be made of any suitable material, but, preferably, is made from a suitable metal, such as, for example, steel, or the like.

The supporting member 5 preferably is of a flat, spider-type construction, FIG. 4, embodying an outer, round ring 20, defining the outer periphery thereof, and an inner, round ring 21 disposed in spaced, concentric relation to the ring 20 and connected thereto by a plurality of spaced legs 22 which define the lateral sides of a plurality of openings 23 extending through the supporting member 5 in surrounding relation to the inner ring 21.

The interior of the passageway 8 in the body portion 3 of the housing 2 has internal threads 24 formed therein. The outer periphery of the outer ring 20 of the supporting member 5 is threaded, and in the assembled respirator 1, the supporting member 5 is threadedly engaged with and held by the internal threads 24 in the passageway 8. Preferably, the supporting member 5 is disposed in the extreme outer end of the end portion of the body member 3 remote from the mouthpiece 7, as shown in FIG. 2.

The inner ring 21 of the supporting member 5 defines a round passageway 25 which extends though the supporting member 5 along the central axis thereof. The ring 21 is of such internal size that it will receive therein suitable tubing for feeding oxygen, such as, for example, a rubber tube 26, FIG. 2, with a slidable, force fit, effective to receive and frictionally hold such a tube, manually inserted therein, while permitting the tube to be manually withdrawn from the ring 21, when desired.

Preferably, the thicknesses of the rings 20 and 21 and the legs 22 are such that the combined areas of the spaces 23 are two-thirds of the transverse area of the passageway 8 in the body portion 3 of the housing 2, and not substantially less than five-ninths of such area; and that the area of the opening 25 through the inner ring 21 is not substantially less than one-sixth and not substantially more than two-ninths of the transverse area of the passageway 8. It has been found that, with this construction, a sufficient flow of air, or a combination of air and oxygen, into the respirator 1, when a person is properly inhaling through the mouthpiece 7 thereof, is insured, so that the end portion 18 of the reed 12 will properly vibrate irrespective of whether or not an oxygen tube is disposed in operative position in the ring 21, and irrespective of whether or not such an oxygen tube is open or closed; and that a sufficient flow of material outwardly through the respirator 1 is insured, when a person properly exhales through the mouthpiece 7 that the end portion 19 of the reed 12 will be caused to properly vibrate under any of the aforementioned conditions.

Thus, in the use of the respirator 1, it may be connected, if desired to a suitable source of oxygen, such as, for example, a tank of medical oxygen, now shown, by a suitable connector member, such as, for example, the tube 26 inserted into operative position in the inner ring 21 of the supporting member 5, as shown in FIGS. 2 and 4. The flow of oxygen from the source of supply through the tube 26 into the respirator 1 may be controlled by suitable controls, such as valves, not shown, in a manner well known in the art. When the respirator 1 is so connected to a source of oxygen, and oxygen is flowing through the tube 26 into the housing 2, and the person using the respirator properly inhales through the mouthpiece 7, the oxygen, mixed with air passing through the openings 23 is inhaled through the respirator 1, into the lungs of the person, and the end portion 18 of the reed 12 is caused to vibrate to thereby vibrate the material passing through the respirator 1. In addition, this vibration causes vibration of the material flowing into the trachea and lungs of the person using the respirator. Subsequently, when the person exhales through the mouthpiece 7, the material thus expelled from the lungs of the person passes longitudinally through the respirator 1 and outwardly through the openings 23 in the supporting member 5. This flow of material, during proper exhalation, is effective to cause vibration of the end portion 19 of the reed 12, with consequent vibration of the material being exhaled through the respirator 1, which vibrations are transmitted to the air, and the like, in the trachea and lungs of the person using the respirator.

Also, it will be seen that, if desired, the respirator 1 may be used without connecting it to a connector, such as the tube 26, and under these conditions air is inhaled through the openings 23 and 25, during each inhalation, and the material expelled from the lungs during an exhalation passes outwardly through the openings 23 and 25. Again, in each instance, the passage of material through the vibrator 9 during inhalation and exhalation is sufficient to cause vibration of the end portions 18 and 19, respectively, of the reed 12.

Also, with the respirator 1 constructed in the aforementioned manner, even if it is connected to a connector such as the tube 26, and the connector is closed against the passage of material therethrough, the passage of air into the respirator 1 though the openings 23 during a proper inhalation through the respirator 1, and the passage of material outwardly through the openings 23 during a proper exhalation through the respirator 1 is effective to cause the aforementioned vibrations of the end portions 18 and 19, respectively, of the reed 12.

A modified form of the present invention is illustrated in FIGS. 5–7, inclusive, of the drawings. This modified form of the invention embodies the same general principles as the preferred form illustrated in FIGS. 1–4, inclusive, and parts which are the same as parts shown in FIGS. 1–4 are indicated by the same reference numerals, and parts which are similar to but which have been substituted for parts shown in FIGS. 1–4 are indicated by the same reference numerals with the suffix "a" added.

The respirator 1a, FIGS. 5 and 6, embodies an elongated, tubular housing 2a, which, like the housing 2 in the respirator 1 embodies an elongated body portion 3a having an end piece or cap 4a mounted on one end thereof. However, unlike the body portion 3 of the housing 2, the body portion 3a of the housing 2a is substantially eliptical in transverse cross section, FIG. 7. The inner end portion 6a of the cap 4a is complimentary in transverse cross sectional shape to the body portion 3a, and the outer end portion of the cap 4a affords a mouthpiece 7, which preferably is of the same size and shape as the mouthpiece 7 of the respirator 1.

Unlike the body portion 3, the body portion 3a has two elongated passageways 27 and 28 extending longitudinally therethrough in parallel relation to each other. The passageways 27 and 28 are separated from each other throughout their length by a partition wall 29, FIGS. 6 and 7, and each is preferably round in transverse cross section. Two vibrators 30 and 31 are mounted in the passageways 27 and 28 respectively. The vibrators 30 and 31 are identical in construction, and each embodies an elongated body portion 10a. Like the body portion 10, each of the body portions 10a has an elongated passageway 11a, which is substantially semicircular in transverse cross section and an elongated channel 13a, which is substantially rectangular in transverse cross section, extending axially therethrough in side-by-side relation to each other.

An elongated reed 32 is mounted in each of the channels 13a. However, unlike the reed 11, the reeds 32 project outwardly from only a single end of the body portion 10a of the respective vibrators 30 and 31. The end portion 18a of the vibrator 30 projects toward the end of the housing 2a remote from the mouthpiece 7, and the end portion 19a of the reed 32 in the vibrator 31 projects toward the mouthpiece 7, FIG. 6.

Also, unlike the body portion 10 of the vibrator 9, the body portions 10a of the vibrators 30 and 31 each have a single tongue 14a and 16a, respectively, projecting outwardly beyond the end of the passageway 11a from which the end portions 18a and 19a, respectively, of the reeds 32 project outwardly. Like the tongues 14 and 15, the tongues 14a and 15a have upper faces 16a and 17a, respectively, thereon which are disposed at an acute angle to the horizontal, as viewed in FIG. 6, in facing relation to the respective outwardly projecting end portions 18a and 19a of the reeds 32.

It is to be observed that although the vibrators 30 and 31 are identical in construction, they are mounted in the respective passageways 27 and 28 in reverse direction relative to each other, the vibrator 30 being disposed in the passageway 27 in such position that the reed 32 thereof projects toward the end portion of the housing 2a remote from the mouthpiece 7, and the vibrator 31 being mounted in the passageway 28 in such position that the reed 32 thereof projects toward the mouthpiece 7.

With the vibrators 30 and 31 constructed in the aforementioned manner and operatively mounted in the respective passageways 27 and 28, air passing through the vibrators 30 and 31 from the end thereof from which the end portions 18a and 19a of the respective reeds 32 project, during proper inhalation and exhalation, respectively, through the respirator 1a, will cause the reeds 32 to be rapidly vibrated and thus cause vibrations to occur in the air in the respirator 1a, and in the air in the trachea and lungs of the person breathing through the respirator 1. Preferably, the vibrators 30 and 31 are of such construction that the frequency of the aforementioned vibrations of the reeds 32 therein is the same as that discussed with respect to the frequency of vibration of the reed 12 of the vibrator 1.

The interiors of the passageways 27 and 28, remote from the mouthpiece 7 have internal threads 24a formed therein. A supporting member 5, which is identical in construction to the supporting member 5 in the respirator 1, is mounted in the extreme outer end of the end portion of the passageway 27, remote from the mouthpiece 7, and is threadly engaged in and held by the threads 24a in the passageway 27.

Unlike the respirator 1, the respirator 1a embodies two one-way valves 33 and 34, which are mounted in the passageways 27 and 28, respectively, in inwardly spaced rotation to the supporting member 5 and the end of the passageway 28 remote from mouthpiece 7, respectively, and in outwardly spaced relation to the vibrators 30 and 31, respectively. Each of the valves 33 and 34 is identical in construction, and each embodies an annular seat 35 having a central opening 36 extending therethrough; a valve member 37 movable into and out of engagement with the respective seat 35; an annular retainer ring 38, having a central opening 39 extending therethrough; and a compression coil spring 40 disposed between the valve member 37 and the seat 35 in position to yieldingly normally hold the valve member 37 in engagement with the seat 35. The outer peripheries of the seats 35 and the retainers 38 are threaded, and in the assembled respirator 1a, the seats 35 and the retainers 38 of the valves 33 and 34 are threadedly engaged with, and held by the internal threads 24a in the passageways 27 and 28, respectively.

Each of the valve members 37 has a round, substantially flat body portion 41, from one side of the outer periphery of which projects an annular flange 42, FIG. 6. The valve members 37 are of such size that, when the faces of the body portions 32 thereof remote from the flanges 42 are disposed in abutting engagement with the respective seats 35, the valve members 37 are effective to close the openings 36 through the latter.

In the assembled valves 33 and 34, the retainers 38 and the seats 35 are disposed in spaced relation to each other, with the valve members 37 disposed therebetween in position wherein the flanges 42 project toward the retainers 38, FIG. 6. The springs 40 are disposed between, and are abuttingly engaged with the retainers 38 and the valve members 37 of the respective valves 33 and 34, and are of such size that they fit into the concavity defined by the flanges 42 on the respective valves 37, FIG. 6.

The valve members 33 and 34, which it will be remembered are identical in construction, are disposed in reverse relation to each other in the passageways 27 and 28, respectively. Thus, the valve member 33 is disposed in the passageway 27 in position wherein the outer face of the seat 35 thereof faces toward the end of the housing 2a remote from the mouthpiece 7; and the valve member 34 is disposed in the passageway 28 in such position that the outer face of the seat 35 thereof faces toward the mouthpiece 7. Thus, when a person is breathing through the mouthpiece 7, he may exhale through the passageway 28 and inhale through the passageway 27, the valves 23 and 24 being effective to prevent inhalation through the passageway 28 and exhalation through the passageway 27. With this construction, the vibrator 30 may be caused to vibrate during inhalation through the respirator 1a, and the vibrator 31 may be caused to vibrate during exhalation through the respirator 1a.

With the seats 35 and retainers 38 of the valves 33 and 34 threadedly mounted in the respective passageways 27 and 28, the seats 35 and the retainers 38 of the respective valves 33 and 34 may be readily adjusted toward and away from each other by rotating the same, to thereby adjust the force with which the respective springs 40 urge the valve members 37 engaged thereby against the adjacent seats 35. Such adjustment is effective to regulate the force with which a person must inhale and exhale through the respirator 1 in order to open the valves 33 and 34, respectively, and thereby cause air to flow through the passageways 27 and 28, respectively, during such inhalation and exhalation.

In the form of the invention shown in FIGS. 5-7, a face piece 43, which is of a type well known in the respirator art, is mounted on the mouthpiece 7 of the cap 4a in surrounding relation thereto. The face piece 43 may be made of any suitable, soft, plyable material, such as, for example, sponge rubber, and flares outwardly from the cp 4a. The facepiece 43 is so disposed on the mouthpiece 7 of the cap 4a, that when the mouthpiece 7 is disposed in operative position in a person's mouth, the face piece 43 is pressed against the face of the person in sealing engagement therewith so as to assist in insuring against leakage between the respirator 1a and the mouth of the person breathing therethrough.

A coupling member 44 having a passageway 45 extending therethrough, FIG. 6, is mounted in and extends through the side wall of the body portion 3a of the housing 2a into the passageway 27, between the vibrator 30 and the cap 4a. If desired, auxiliary material, such as, for example, a medicant spray or gas may be fed through the passageway 45 into the passageway 27 while a person is using the respirator, so that the auxiliary material mixes with the main material, such as for example, the aforementioned air or mixture of air and oxygen passing into the respirator 1a through the end portion of the passageway 27 remote from the mouthpiece 7, and is inhaled with the main material into the lungs of the person using the respirator 1a.

The various parts of the respirator 1a, corresponding to parts of the respirator 1, preferably are made from the same materials as heretofore set forth with respect to the respirator 1. In addition, the valves 33 and 34 may be made of any suitable material, but, preferably are made from a suitable metal, such as, for example, steel, or the like.

The supporting member 5, embodied in the respirator 1a is identical to the supporting member 5 embodied in the respirator 1, and is operable, and functions in the same manner as the supporting member 5 in the respirator 1. Thus, a connector, such as the tube 26 may be selectively mounted in the supporting member 5 for feeding oxygen into the inhalation passageway 27, supplemental air being drawn in through the passageway 23, surrounding the tube 26, during inhalation through the respirator 1a; and, also, the respirator 1a will fully function with air, only, inhaled through the supporting member 5 irrespective of whether a connector, such as the tube 26 is disposed in the supporting member 5 and whether the tube 26 is open or closed for the passage of oxygen, or the like therethrough.

Another modified form of the present invention is illustrated in FIGS. 8-13, inclusive, of the drawings. This modified form of the invention is identical in construction to the form of the invention shown in FIGS. 5-7, inclusive, except for the manner in which it may be connected to an outside source of oxygen and the manner in which air may be fed into the respirator, and parts which are the same as parts shown in FIGS. 5-7 are indicated by the same reference numerals, and parts which are similar to but which have been substituted for parts shown in FIGS. 5-7 are indicated by the same reference numerals with the suffix "b" added.

It will be remembered that the respirator 1b shown in FIGS. 8-13, is identical in construction to the respirator 1a, shown in FIGS. 1-7, except for the structure by which air and oxygen may be fed thereinto. In the respirator 1b, the supporting member 5b comprises the end portion of that portion of the body member 3a of the housing 2b thereof, which defines the end of the passageway 27 remote from the mouthpiece 7, FIG. 9. A plurality of spaced openings 23b are formed through the side wall of the body portion 3a into the passageway 27, FIGS. 9 and 13. The openings 23b are disposed in a substantially semi-circular shaped pattern to the right of the vertical center line through the passageway 27, as viewed in FIG. 13, and are disposed in the end portion of the body portion 3a remote from the mouthpiece 7, in inwardly spaced relation to the outer extremity thereof. Like the passageways or openings 23, the passageways 23b are of such size and number that the total transverse areas thereof are two-thirds, and not substantially less than five-ninths of the transverse area of the passageway 27. If desired, of course, a plurality of rows of the openings 23b may be used instead of the single row shown herein, or a single opening or slot of sufficient size may be substituted for the plurality of openings 23b.

The spacing of the passageways 23b from the end of the passageway 27 remote from the mouthpiece 7 is such that a suitable connector, such as the tube 26b, may be inserted into the end of the passageway 27, outwardly of the passageways 23b a sufficient distance to firmly, operably hold the tube 26b in position therein, in outwardly spaced relation to the passageways 23b, as shown in FIG. 9. With this construction, and when oxygen is passing through the tube 26b into the passageway 27 in the respirator 1b from a source of oxygen supply, not shown, when a person using the respirator 1b properly inhales through the mouthpiece 7, air flows inwardly through the passageways 23b from the surrounding atmosphere and mixes with the oxygen flowing through the tube 26a, with the mixture passing through the valve 33 and the vibrator 30 into the lungs of the person using the respirator. When the person exhales through the respirator 1b, the material exhaled passes outwardly through the vibrator 31 and the valve 34 mounted in the passageway 28, the valve 33 being held closed by its spring 40.

With the respirator 1b constructed in the aforementioned manner, it is, like the respirator 1a, operable to effectively vibrate material passing therethrough during proper inhalation and exhalation through the mouthpiece 7, the flow of air inwardly through the passageways 23b, during inhalation, being sufficient to enable such vibration to be effected, irrespective of whether a tube, such as the tube 26a is mounted in the respirator 1b, and irrespective of whether such a tube, when such a tube is mounted in the respirator 1b, is open or closed for the passage of oxygen therethrough. Of course, the respirator 1b may also be used without any member, such as the tube 26a, being connected thereto, and in such operation, air not only flows inwardly through the passageways 23b during inhalation, but also inwardly through the unrestricted end of the passageway 27, remote from the mouthpiece 7.

From the foregoing it will be seen that the present invention affords a novel respirator which is effective, in a novel and expeditious manner, to feed either air or a mixture of oxygen and air therethrough.

In addition, it will be seen that the present invention affords a novel respirator which is effective to pass either air or a mixture of air and oxygen therethrough, and in which the material passing through the respirator is caused to vibrate in such a manner as to vibrate the air in the trachea and lungs of a person breathing through the respirator, during both inhalation and exhalation through the respirator.

Also, it will be seen that the present invention affords a novel respirator which affords a novel device for vibrating the cilia in the lungs of a patient using the same.

In addition, it will be seen that the present invention affords a novel respirator of the aforementioned type, which is practical and efficient in operation, and which may be readily and economically produced commercially.

Thus, while I have illustrated and described the preferred embodiments of my invention, it is to be understood that these are capable of variation and modification, and I therefore do not wish to be limited to the precise details set forth, but desire to avail myself of such changes and alterations as fall within the purview of the following claims.

I claim:

1. A respirator of the type adapted to be connected by a tube to a supply source of oxygen, said respirator comprising
   a. an elongated housing having a first end and a second end and having a passageway extending longitudinally therethrough and being of a size and shape adapting it to be carried in the hand of a person, and having a mouthpiece on said first end thereof communicating with said passageway for insertion into said person's mouth and means within said passageway to thereby enable the person to
      1. inhale in one direction longitudinally through said passageway and from said second end to said first end, and
      2. exhale longitudinally through said passageway in the direction opposite to said one direction and from said first end to said second end,
   b. means within said passageway between said first and second ends for vibrating material inhaled and exhaled therethrough, and
   c. other means at said second end of said housing, for supportingly holding an end of such an oxygen tube in position in a portion of said other means to feed oxygen from such a supply source into said passageway,
   d. said other means having a passage means therethrough for the passage of air into and out of said passageway exteriorly of such a tube disposed in said position in said portion.

2. A respirator as defined in claim 1, and in which
   a. said other means comprises a supporting member
      1. disposed at said other end of said housing,
      2. having an opening therethrough for receiving such an end of a tube therein for so supportingly holding said tube end, and
      3. having another opening therethrough in outwardly disposed relation to said last mentioned opening.

3. A respirator of the type adapted to be connected by a tube to a supply source of oxygen, said respirator comprising
   a. an elongated housing having a first end and a second end and having a passageway extending therethrough having a mouthpiece on said first end thereof communicating with said passageway for insertion into a person's mouth and means within said passageway to thereby enable the person to
      1. inhale in one direction longitudinally through said passageway and from said second end to said first end, and
      2. exhale longitudinally through said passageway in the direction opposite to said one direction and from said first end to said second end,
   b. means within said passageway between said first and second ends for vibrating material inhaled and exhaled therethrough, and
   c. other means at said second end of said housing, for supportingly holding an end of such an oxygen tube in position in a portion of said other means to feed oxygen from such a supply source into said passageway,
   d. said other means having a passage means therethrough for the passage of air into and out of said passageway exteriorly of such a tube disposed in said position in said portion,
   e. said other means comprising a supporting member
      1. disposed at said said end of said housing,
      2. having an opening therethrough for receiving such an end of a tube therein for so supportingly holding said tube end, and
      3. having openings therethrough in radially outwardly disposed relation to said last mentioned openings.

4. A respirator of the type adapted to be connected by a tube to a supply source of oxygen, said respirator comprising
   a. an elongated housing having a first end and a second end and having a passageway extending therethrough having a mouthpiece on said first end thereof communicating with said passageway for insertion into a person's mouth and means within said passageway to thereby enable the person to
      1. inhale in one direction longitudinally through said passageway and from said second end to said first end, and
      2. exhale longitudinally through said passageway in the direction opposite to said one direction and from said first end to said second end,
   b. means within said passageway between said first and second ends for vibrating material inhaled and exhaled therethrough, and
   c. other means at said second end of said housing, for supportingly holding an end of such an oxygen tube in position in a portion of said other means to feed oxygen from such a supply source into said passageway,
   d. said other means having a passage means therethrough for the passage of air into and out of said passageway exteriorly of such a tube disposed in said position in said portion,
   e. said other means comprising a supporting member
      1. disposed at said second end of said housing,
      2. having an opening therethrough for receiving such an end of a tube therein for so supportingly holding said tube end, and
      3. having another opening therethrough in outwardly disposed relation to said last mentioned opening,
   f. said supporting member comprising a spider
      1. mounted in said second end of said housing,
      2. having a substantially centrally disposed opening therethrough for receiving such an end of a tube therein for so supportingly holding said tube end, and
      3. having a plurality of other opeings therethrough in substantially surrounding relation to said centrally disposed opening.

5. A respirator of the type adapted to be connected by a tube to a supply source of oxygen, said respirator comprising
   a. an elongated housing having a first end a second end and having a passageway extending therethrough having a mouthpiece on said first end thereof communicating with said passageway for insertion into a person's mouth and means within said passageway to thereby enable the person to
      1. inhale in one direction longitudinally through said passageway and from said second end to said first end, and 2. exhale longitudinally through said passageway in the direction opposite to said one direction and from said first end to said second end,
b. means within said passageway between said first and second ends for vibrating material inhaled and exhaled therethrough, and
c. other means at said second end of said housing, for supportingly holding an end of such an oxygen tube in position in a portion of said other means to feed oxygen from such a supply source into said passageway,
d. said other means having a passage means therethrough for the passage of air into and out of said passageway exteriorly of such a tube disposed in said position in said portion,
e. said other means comprising a supporting member
   1. disposed at said second end of said housing,
   2. having an opening therethrough for receiving such an end of a tube therein for so supportingly holding said tube end, and
   3. having another opening therethrough in outwardly disposed relation to said last mentioned opening,
f. said supporting member comprising the end portion of said housing remote from said first end thereof, and
g. said other opening extending through said end portion of said housing in position to be disposed between said tube end and said first mentioned means when said tube end is so disposed in said first mentioned opening in said supporting member.

6. A respirator of the type adapted to be connected by a tube to a supply source of oxygen, said respirator comprising
a. an elongated housing having a first end a second end and having a passageway extending therethrough having a mouthpiece on said first end thereof communicating with said passageway for insertion into a person's mouth and means within said passageway to thereby enable the person to
   1. inhale in one direction longitudinally through said passageway and from said second end to said first end, and
   2. exhale longitudinally through said passageway in the direction opposite to said one direction and from said first end to said second end,
b. means within said passageway between said first and second ends for vibrating material inhaled and exhaled therethrough, and
c. other means at said second end of said housing, for supportingly holding an end of such an oxygen tube in position in a portion of said other means to feed oxygen from such a supply source into said passageway,
d. said other means having a passage means therethrough for the passage of air into and out of said passageway exteriorly of such a tube disposed in said position in said portion,
e. said other means comprising the end portion of said housing remote from said first end thereof, and
f. said passage means comprising a plurality of spaced openings through said end portion in position to be disposed between such a tube end and said first mentioned means when said tube end is so supportingly held by said other means for feeding air into said passageway during such inhalation.

7. A respirator of the type adapted to be connected by a tube to a supply source of oxygen, said respirator comprising
a. an elongated tubular housing having a mouthpiece at one end thereof for insertion into a person's mouth and means within said housing to thereby enable the person to
   1. inhale in one direction longitudinally through said housing, and
   2. exhale longitudinally through said housing in the direction opposite to said one direction,
b. means within said housing for vibrating material inhaled and exhaled therethrough, and
c. other means at the other end of said housing, at the opposite side of said first mentioned means from said mouthpiece, for supportingly holding an end of such an oxygen tube in position in a portion of said other means to feed oxygen from such a supply source into said housing,
d. said other means having a passage means therethrough for the passage of air into and out of said housing exteriorly of such a tube disposed in said position in said portion,
e. said first mentioned means comprising
   1. a body portion
      a. mounted in said housing between said other means and said one end of said housing and
      b. having an opening extending therethrough in substantially axial relation to said housing for the passage of material therethrough during such inhalation and exhalation, and
   2. a reed
      a. disposed in said body portion along one side of said opening, and
      b. having end portions projecting outwardly from respective opposite sides of said body portion.

8. A respirator of the type adapted to be connected by a tube to a supply source of oxygen, said respirator comprising
a. an elongated tubular housing having a mouthpiece at one end thereof for insertion into a person's mouth and means within said housing to thereby enable the person to
   1. inhale in one direction longitudinally through said housing, and
   2. exhale longitudinally through said housing in the direction opposite to said one direction,
b. means within said housing for vibrating material inhaled and exhaled therethrough, and
c. other means at the other end of said housing, at the opposite side of said first mentioned means from said mouthpiece, for supportingly holding an end of such an oxygen tube in position in a portion of said other means to feed oxygen from such a supply source into said housing,
d. said other means having a passage means therethrough for the passage of air into and out of said housing exteriorly of such a tube disposed in said position in said portion,
e. said housing having two passageways extending longitudinally through at least a portion thereof,
f. said means for vibrating material inhaled through said housing being mounted in one of said passageways,
g. said means for vibrating material exhaled through said housing being mounted in the other of said passageways, and h. said other means being disposed at the end of said one passageway remote from said one end of said housing.

9. A respirator of the type adapted to be connected by a tube to a supply source of oxygen, said respirator comprising
   a. an elongated tubular housing having a mouthpiece at one end thereof for insertion into a person's mouth and means within said housing to thereby enable the person to
      1. inhale in one direction longitudinally through said housing, and
      2. exhale longitudinally through said housing in the direction opposite to said one direction,
   b. means within said housing for vibrating material inhaled and exhaled therethrough, and
   c. other means at the other end of said housing, at the opposite side of said first mentioned means from said mouthpiece, for supportingly holding an end of such an oxygen tube in position in a portion of said other means to feed oxygen from such a supply source into said housing,
   d. said other means having a passage means therethrough for the passage of air into and out of said housing exteriorly of such a tube disposed in said position in said portion,
   e. said first mentioned means comprising
      1. supporting means mounted in said housing between said one end and said other end thereof and having passageway means therethrough for the passage of material between said ends of said housing, and
      2. reed means mounted in said passageway means and projecting from said supporting means in a direction to vibrate material passing through said passageway means.

10. A respirator of the type adapted to feed a mixture of oxygen and atmospheric air therethrough, said respirator comprising
   a. an elongated tubular housing of a size and shape adapting it to be carried in the hand of a person, and having one end for insertion into the mouth of said person and means within said housing to thereby enable the person to inhale in one direction and exhale in the opposite direction longitudinally through said housing,
   b. means at the other end of said housing for
      1. feeding material into said housing for inhalation by such a person through said one end and
      2. feeding exhaled material outwardly from said housing when such exhaled material is exhaled by such a person through said one end, and
   c. means within said housing between said one end and said first mentioned means for vibrating said material at a frequency audible to the human ear during said inhalation and exhalation thereof through said housing,
   d. said first mentioned means comprising
      1. a portion adapted to support conduit means in operative position relative to said other end effective to feed oxygen into said other end during such an inhalation, and
      2. passageways disposed in position effective to feed atmospheric air into said other end in position to be mixed with such oxygen during such an inhalation,
   e. said passageways having a total transverse area not substantially less then five-ninths of the maximum transverse area of the interior portion of said housing through which such material passes during such an inhalation.

* * * * *

UNITED STATES PATENT OFFICE
CERTIFICATE OF CORRECTION

Patent No. 4,062,358            Dated December 13, 1977

Inventor(s)   Richard W. Kritzer

It is certified that error appears in the above-identified patent and that said Letters Patent are hereby corrected as shown below:

Column 4, line 47, change "non" to --not--;

Column 8, line 64, change "cp" to --cap--;

Claim 3, column 12, line 4, change "said", second instance, to --second--;

Claim 5, line 4, after "end" insert --and--; and

Claim 6, line 4, after "end" insert --and--.

Signed and Sealed this

Sixteenth Day of May 1978

[SEAL]

Attest:

RUTH C. MASON
Attesting Officer

LUTRELLE F. PARKER
Acting Commissioner of Patents and Trademarks